United States Patent [19]

Tigani

[11] 4,163,318
[45] Aug. 7, 1979

[54] DEVICE FOR REPLACING MISSING TEETH IN HUMAN DENTITION

[76] Inventor: Pasquale Tigani, 5219 Ridgefield Rd., Washington, D.C. 20016

[21] Appl. No.: 779,852

[22] Filed: Mar. 21, 1977

[51] Int. Cl.² .............................................. A61C 13/30
[52] U.S. Cl. ........................................................... 32/5
[58] Field of Search ................................ 32/5, 6, 14 E

[56] References Cited

U.S. PATENT DOCUMENTS

| | | | |
|---|---|---|---|
| 1,211,494 | 1/1917 | Shaw | 32/6 |
| 1,465,473 | 8/1923 | Hansen | 32/5 |
| 1,664,433 | 4/1928 | Seabrook | 32/5 |
| 2,002,048 | 5/1935 | Thomas | 32/5 |
| 2,572,714 | 10/1951 | Funderburg, Jr. | 32/6 |

FOREIGN PATENT DOCUMENTS

| | | | |
|---|---|---|---|
| 352456 | 4/1961 | Switzerland | 32/14 E |
| 641139 | 8/1950 | United Kingdom | 32/14 E |

*Primary Examiner*—Louis G. Mancene
*Assistant Examiner*—John J. Wilson

*Attorney, Agent, or Firm*—Sughrue, Rothwell, Mion, Zinn and Macpeak

[57] ABSTRACT

The device which is adapted to be secured between two existing teeth is suitable for supporting an artificial denture to replace an anterior tooth or a posterior tooth. The device is comprised of a backing member having a pair of parallel extendable arms slidably disposed in grooves in said backing member on opposite sides of a pinion rotatably mounted in said backing member in simultaneous meshing engagement with teeth on both arms for simultaneously extending both arms in opposite directions upon rotation of said pinion in one direction. The extended end of each arm is adapted to be disposed in a precut groove in an existing tooth to support the device between two existing teeth. Suitable projections are provided on the surface of the backing member for cooperation with complimentary grooves in the artificial facing. The facing is secured to the backing and the extended arms are secured in the grooves of adjacent teeth by a suitable cement or filling material.

1 Claim, 6 Drawing Figures

DEVICE FOR REPLACING MISSING TEETH IN HUMAN DENTITION

BACKGROUND OF THE INVENTION

1. Field of the Invention

The present invention is directed to an artificial denture and more specifically to the means for anchoring the artificial denture between two existing teeth.

2. Prior Art

It is old and well known in the artificial denture art to permanently secure a bridge in two oposed grs in spaced apart existing teeth and to secure the artificial tooth or teeth to the bridge in a rein are of a considerable magnitude and frequently have to be undercut in order to provide a complimentary interfitting engagement with enlarged projections on the opposite ends of the bridge. a protruding post or bracket into spaced apart existing natural teeth and detachably or permanently securing the bridge to the protruding post or bracket. Once again it is usually possible to anchor such a post or bracket in the relatively large posterior teeth but extremely difficult if not impossible to anchor such a post or bracket to the anterior teeth. While the use of telescopically adjustable bridge support elements is old and well known in the art the telescopic adjustment must generally take place prior to the insertion of the bridge support device into the complimentary grooves in the spaced apart existing teeth. Thus it is extremely difficult to obtain and maintain the proper telescopic relationship prior to the insertion of the device and during the subsequent removal of the bridge for fitting the facings on the bridge prior to the permanent anchoring of the bridge in the existing teeth.

SUMMARY OF THE INVENTION

The present invention provides a backing device for an artificial denture having readily expansible and contractable anchoring means which can be moved into and out of opposing grooves in spaced apart existing teeth with a minimum of effort and which will maintain their adjusted position until such time as the anchoring means can be permanently secured to the existing teeth.

The present invention provides a backing device for artificial dentures which is adapted to be secured to spaced apart existing teeth in a manner which requires minimal cutting of the existing teeth so as not to structurally weaken the existing teeth or to provide unduly deep cuts which would lead to the early decay and destruction of the existing teeth.

The present invention provides a backing device for artificial dentures having readily adjustable anchoring means suitable for engagement with relatively thin anterior teeth as well as posterior teeth.

The present invention provides a device suitable for replacing missing teeth in human dentition comprising a backing member adapted to be disposed between two spaced apart existing teeth, groove means disposed in said backing member and opening outwardly in opposite directions on opposite sides of said backing member, a pair of arms slidably mounted in said groove means in spaced parallel relation to each other, teeth means formed in the opposing surfaces of the parallel spaced apart portions of said arms, pinion means rotatably mounted in said backing member in meshing engagement with the teeth on each of said arms and means for rotating said pinion means and frictionally holding said pinion means in an adjusted rotational position whereby upon rotation of said pinion in one direction said arms will move outwardly in opposite directions into engagement with adjacent existing teeth and upon rotation of said pinion means in the opposite direction will retract said arms in opposite directions within said groove means in said backing member.

The foregoing and other objects, features and advantages of the invention will be apparent from the following more particular description of preferred embodiments of the invention as illustrated in the accompanying drawings.

DETAILED DESCRIPTION OF THE INVENTION

The artificial denture arrangement according to the present invention is suitable for a connection between two spaced apart existing teeth which may be posterior teeth, anterior teeth, or one of each. The present invention is disclosed in the present application only with respect to situations where a single tooth is missing but it is obvious that the size of the device could be varied to provide support for a plurality of artificial teeth.

Figure 1:
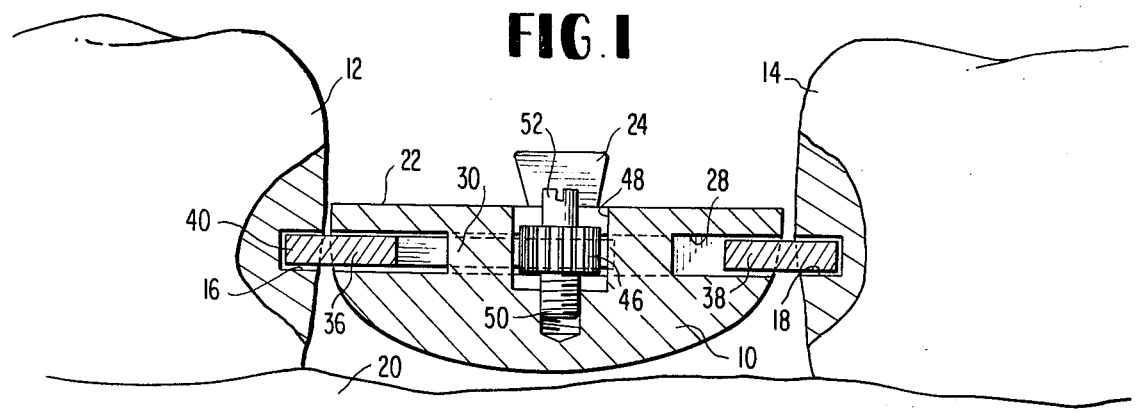
FIG. 1 is a vertical cross-sectional view of the backing device according to the present invention secured between two existing teeth with the facing removed.

The backing member 10 of FIG. 1 is shown disposed between two spaced apart existing posterior teeth 12 and 14. A pair of small opposed grooves 16 and 18 are cut into teeth 12 and 14 respectively transversely to the direction of growth of the teeth. The backing member 10 which is constructed of chrome cobalt metal, stainless steel or any other suitable material has a general outline in section similar to that of the tooth which it is to replace as best seen in FIG. 2 while the underside of the member 10 is merely rounded off as best seen in FIG. 1 and is adapted to be disposed in close proximity to the gum 20.

The backing member 10 is provided with a flat upper surface 22 having one or more projections 24 extending upwardly therefrom and adapted to be disposed in mating relation with a complimentary groove in the standard facing 26 which may be of any suitable material such as porcelain, gold, or the like. The facing 26 may be secured to the backing member 10 by any suitable dental cement.

A transverse groove 28 extends through the backing member 10 from one side to the other. As best seen in FIGS. 1 and 2 a central post portion 30 is left in the center of the device which effectively defines two narrow parallel grooves 32 and 34. A pair of identical arms 36 and 38 are slidably disposed in the groove 28. Each arm is comprised of an anchoring end portion 40 and a narrow operating portion 42 disposed in the slots 32 and 34. The operating portions are provided with a plurality of teeth 44 which are adapted to be disposed in meshing engagement with a pinion 46 rotatably mounted in a cylindrical recess 48 extending into the backing member 10 from the upper surface 22 thereof. The pinion 46 may be integrally secured to a screw member 50 having a slotted operating head 52.

Figure 2:
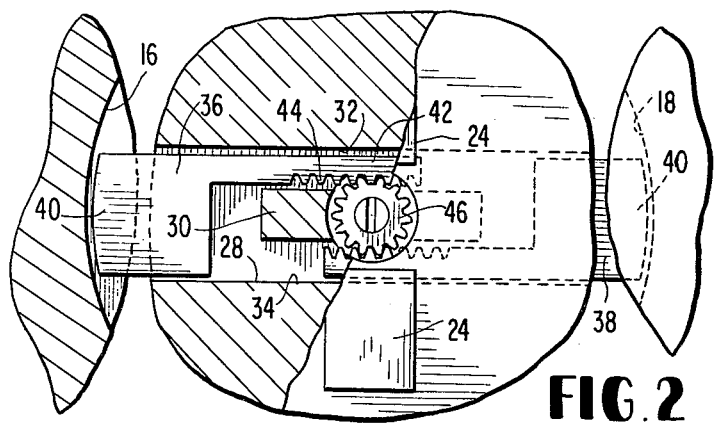
FIG. 2 is a top plan view of the device of FIG. 1 with a portion of the device broken away.

Upon rotation of the screw 50 in a counterclockwise direction as viewed in FIG. 2 the arms 36 and 38 will be moved outwardly in opposite directions so that the anchoring portions 40 will engage in the grooves 16 and 18 formed in the existing adjacent teeth 12 and 14, respectively. The ends of the anchoring portions should have a complimentary configuration to the grooves 16 and 18 but may be provided with a serrated edge (not shown) in order to bite into the tooth material to more firmly anchor the backing device between the two existing teeth. The frictional threaded engagement of the screw 50 will provide a self-locking arrangement so that the arms 36 and 38 will remain in their adjusted positions. If it is necessary to remove the backing member 10 for further work it is only necessary to rotate the pinion 46 in the clockwise direction as viewed in FIG. 2 in order to retract the arms 36 and 38 into the groove 28 so as to withdraw the anchoring portions 40 from the grooves 16 and 18 in the adjacent existing teeth.

Figure 3:
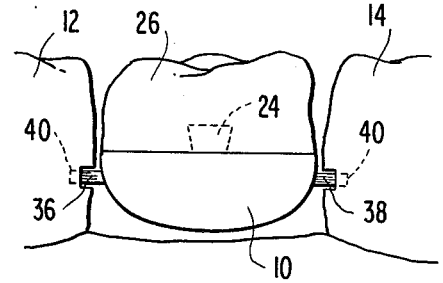
FIG. 3 is a side elevation view of a complete artificial denture according to the present invention secured between two adjacent posterior teeth.
Figure 4:
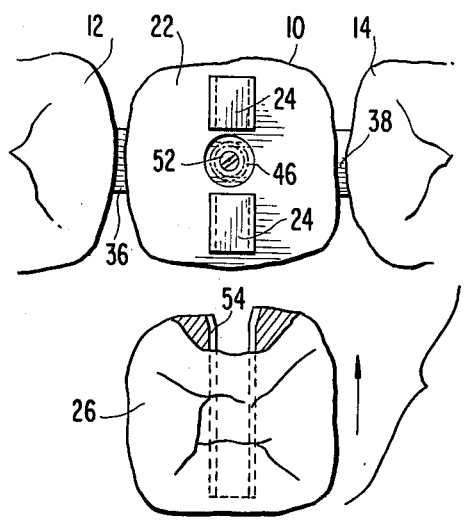
FIG. 4 is a top plan view of the artificial denture shown in FIG. 3 with the artificial facing disposed to one side in a line positioned for securement to the backing device.

Once the preliminary work is finished and it is desired to permanently anchor the backing member 10 between the two existing teeth 12 and 14, the pinion 46 will be rotated in the counterclockwise direction as viewed in FIG. 2 to fully extend the anchoring portions 40 of the two arms 36 and 38 into the grooves 16 and 18 in the existing teeth. A suitable dental cement or filling material would then be applied to fill the grooves 16 and 18 and anchor the ends of the arms 36 and 38 in the grooves. The cap or facing 26 which is provided with a groove 54 complimentary to the projections 24 is then aligned with the projections 24 as seen in FIG. 4 and then slid onto the projections 24 in the direction of the arrow. The projections 24 and the groove 54 as well as the opposing surfaces of the backing member 10 and the cap or facing 26 may be coated with any suitable dental cement or adhesive so that the cap or facing 26 will be permanently secured to the backing member 10 as seen in FIG. 3 while the backing member 10 is permanently secured between the two teeth 12 and 14.

Figure 5:
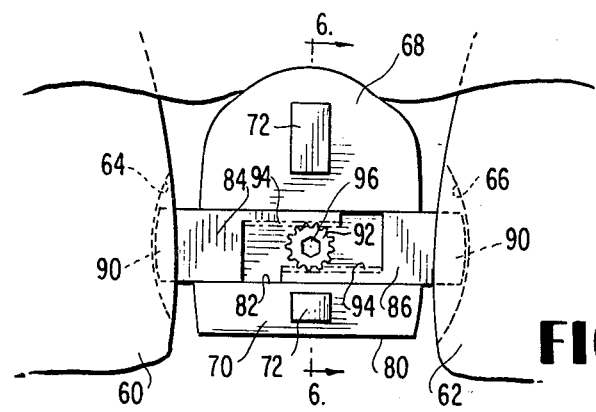
FIG. 5 is a front elevation view of a modified form of backing device according to the present invention for engagement between two existing anterior teeth.
Figure 6:
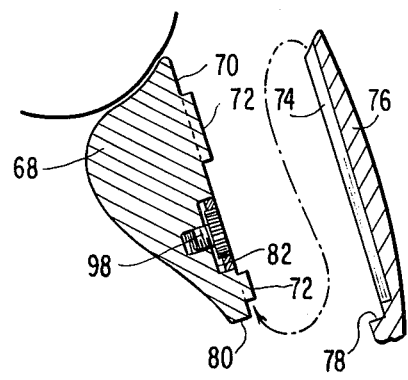
FIG. 6 is a sectional view taken along the line 6—6 in FIG. 5.

While the foregoing embodiment was described with respect to a replacement denture for posterior teeth the embodiment of FIGS. 5 and 6 show a suitable replacement denture device for use between two anterior teeth. Since the anterior teeth 60 and 62 are relatively thin the proposed grooves 64 and 66 are cut into the teeth in the direction of growth of the teeth. The backing member 68 is provided with a flat frontal surface 70 having a suitable projection 72 thereon adapted to be disposed in mating engagement in a complimentary recess 74 formed in the cap or facing 76. The cap or facing 76 is provided with an angled bottom portion 78 adapted to fit under the edge 80 of the backing member 68 so that the backing member 68 will not ordinarily be visible when the cap or facing 76 is secured thereto. Since the backing member 68 is relatively shallow as compared to the backing member 10 in the previous embodiment, the groove 82 may be machined directly into the front face 70 of the backing member 68. A pair of identical arms 84 and 86 similar to the arms 36 and 38 are slidably disposed within the groove 82 with the anchoring ends 90 having a complimentary configuration for engagement in the grooves 64 and 66 of the existing teeth. A pinion 92 is rotatably mounted within the groove 82 in meshing engagement with the teeth 94 formed on the arms 84 and 86 as in the previous embodiment. In view of the shallow nature of the groove 82 a socket 96 may be provided in the upper surface of the screw 98 for operative engagement by an Allen wrench.

As in the previous embodiment the rotation of the pinion 92 in the counterclockwise direction as viewed in FIG. 5 will move the arms 84 and 86 in opposite directions so that the anchoring portions 90 will be disposed in engagement in the grooves 64 and 66 of the teeth 60 and 62, respectively. When it is desired to permanently anchor the backing member 68 in the grooves a suitable dental cement or filling material may be applied to the grooves 64 and 66 to anchor the arms 84 and 86 therein permanently. A suitable adhesive may be used to permanently secure the cap or facing member 76 to the front face 70 of the backing member 68.

In both embodiments the securement of the cap in place upon the backing member will completely cover the pinion for operating the anchoring arms. The exact configuration of the anchoring arms as well as the grooves in which they are disposed may vary within the scope of the present invention and any suitable materials conventional in artificial denture work may be used for the parts of the present invention.

While the invention has been particularly shown and described with reference to preferred embodiments thereof it will be understood by those in the art that the foregoing and other changes in form and details may be made therein without departing from the spirit and scope of the invention.

What is claimed is:

1. An artificial denture device comprising a backing member having a flat surface adapted to be disposed between two spaced apart existing teeth, groove means disposed in said backing member and opening outwardly in opposite directions on opposite sides of said backing member, a pair of arms slidably mounted in said groove means in spaced parallel relation to each other and said flat surface, operating means comprised of a screw member threaded into said backing member for rotation about an axis perpendicular to said flat surface between said arms, engaging means on said arms and said operating means for moving said arms in opposite directions upon rotation of said operating means for engaging the outer ends of said arms in opposed grooves in spaced apart existing teeth and facing means secured to said flat surface of said backing member to cover said operating means.

* * * * *